US006976386B1

(12) United States Patent     (10) Patent No.:   US 6,976,386 B1
Grover et al.     (45) Date of Patent:   Dec. 20, 2005

(54) TENSIOMETER METHODS

(75) Inventors: Blair K. Grover, Idaho Falls, ID (US); Joel M. Hubbell, Idaho Falls, ID (US); James B. Sisson, Idaho Falls, ID (US); William L. Casper, Rigby, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 10/873,975

(22) Filed: Jun. 22, 2004

Related U.S. Application Data

(62) Division of application No. 10/286,709, filed on Oct. 31, 2002, now Pat. No. 6,772,621.

(51) Int. Cl.$^7$ ............................ E21B 49/08; G01L 7/18
(52) U.S. Cl. ...................... 73/73; 73/29.02; 73/152.05; 73/152.06; 73/152.41; 73/152.54; 137/78.2; 137/78.3
(58) Field of Search .............................. 73/73, 152.05, 73/152.06, 152.41, 152.54, 19.09, 29.02; 137/78.2, 78.1, 78.3; 175/52, 56, 57

(56) References Cited

U.S. PATENT DOCUMENTS

| 3,043,133 | A | * | 7/1962 | Richards ......................... 73/73 |
| 3,049,914 | A | * | 8/1962 | Richards ......................... 73/73 |
| 3,103,117 | A | * | 9/1963 | Richards ......................... 73/73 |
| 3,871,211 | A | * | 3/1975 | Tal ................................. 73/73 |
| 3,898,872 | A | | 8/1975 | Skaling et al. |
| 3,910,300 | A | | 10/1975 | Tal |
| 3,939,699 | A | * | 2/1976 | McCormick ................... 73/73 |
| 3,961,753 | A | | 6/1976 | Sears |
| 4,068,525 | A | | 1/1978 | Skaling |
| 4,137,931 | A | * | 2/1979 | Hasenbeck ................. 137/78.3 |
| 4,655,076 | A | | 4/1987 | Weihe et al. |
| 4,669,554 | A | * | 6/1987 | Cordry ......................... 175/59 |
| 4,679,422 | A | | 7/1987 | Rubin et al. |
| 4,845,978 | A | * | 7/1989 | Whitford ....................... 73/73 |
| 4,922,945 | A | | 5/1990 | Browne |
| 5,000,051 | A | * | 3/1991 | Bredemeier ............... 73/863.23 |
| 5,156,179 | A | | 10/1992 | Peterson et al. |
| 5,179,347 | A | | 1/1993 | Hawkins |
| 5,465,628 | A | * | 11/1995 | Timmons ................. 73/864.34 |

(Continued)

FOREIGN PATENT DOCUMENTS

GB     2137760 A    *   10/1984     .......... G01N 33/24

(Continued)

OTHER PUBLICATIONS

"Long Term Stewardship Technology Analysis of the Office of Science and Technology Profile", INEEL, 2001, pp. 1-235.*

Primary Examiner—Hezron Williams
Assistant Examiner—David A. Rogers
(74) Attorney, Agent, or Firm—Wells, St. John P.S.

(57) ABSTRACT

A method for collecting data regarding a matric potential of a media includes providing a tensiometer having a stainless steel tensiometer casing, the stainless steel tensiometer casing comprising a tip portion which includes a wetted porous stainless steel membrane through which a matric potential of a media is sensed; driving the tensiometer into the media using an insertion tube comprising a plurality of probe casing which are selectively coupled to form the insertion tube as the tensiometer is progressively driven deeper into the media, wherein the wetted porous stainless steel membrane is in contact with the media; and sensing the matric potential the media exerts on the wetted porous stainless steel membrane by a pressure sensor in fluid hydraulic connection with the porous stainless steel membrane. A tensiometer includes a stainless steel casing.

8 Claims, 8 Drawing Sheets

U.S. PATENT DOCUMENTS

| | | |
|---|---|---|
| 5,644,947 A | 7/1997 | Hubbell et al. |
| 5,758,538 A | 6/1998 | Hubbell et al. |
| 5,941,121 A | 8/1999 | Faybishenko |
| 6,263,726 B1 | 7/2001 | Hubbell et al. |
| 6,308,563 B1 | 10/2001 | Hubbell et al. |
| 6,539,780 B2 | 4/2003 | Hubbell et al. |

FOREIGN PATENT DOCUMENTS

| | | | | |
|---|---|---|---|---|
| GB | 2137760 A | | 10/1987 | |
| GB | 2249182 A | * | 4/1992 | .......... G01N 33/24 |
| JP | 63030743 A | * | 2/1988 | .......... G01N 19/10 |
| WO | WO 9804915 A1 | | 2/1998 | |

* cited by examiner

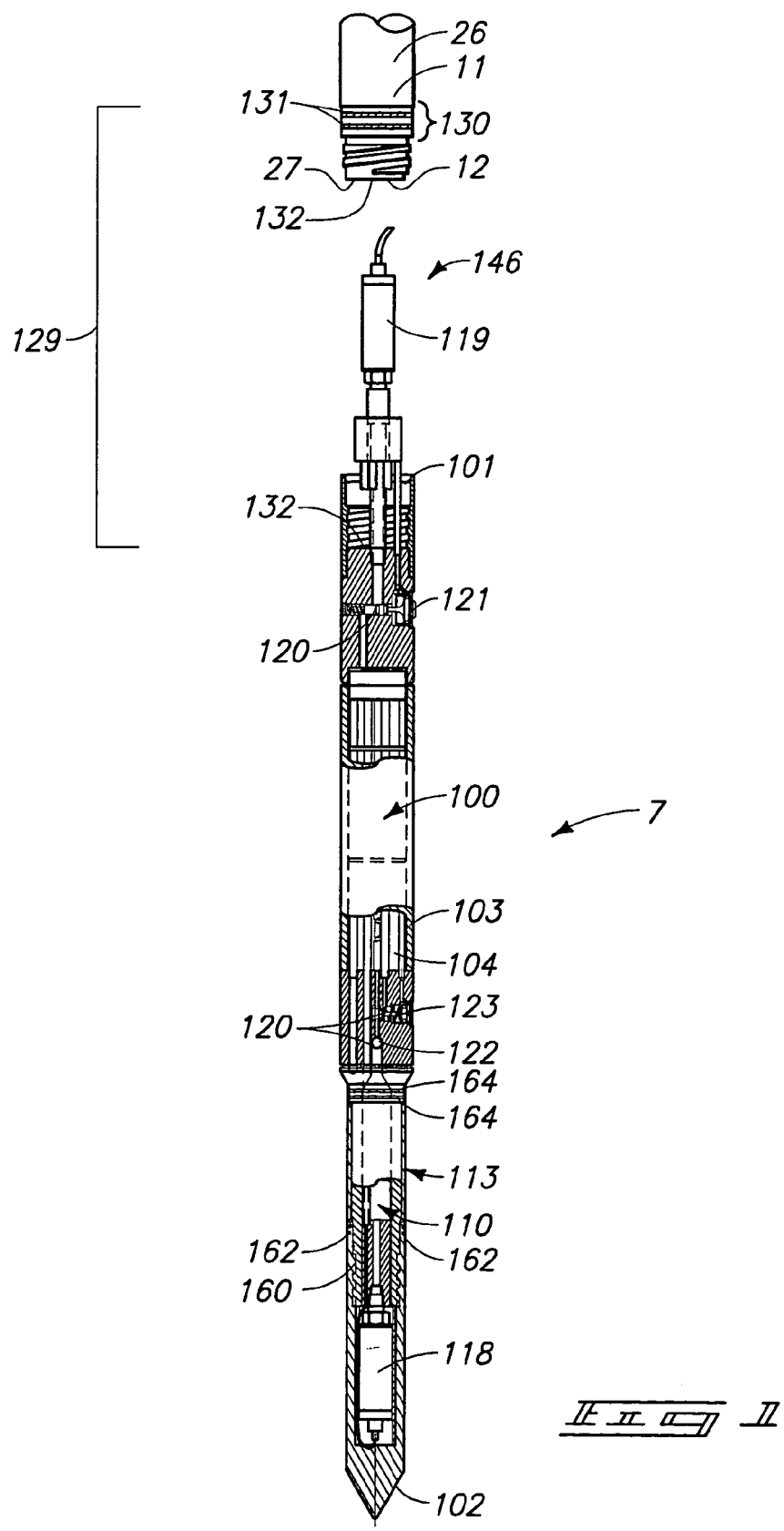

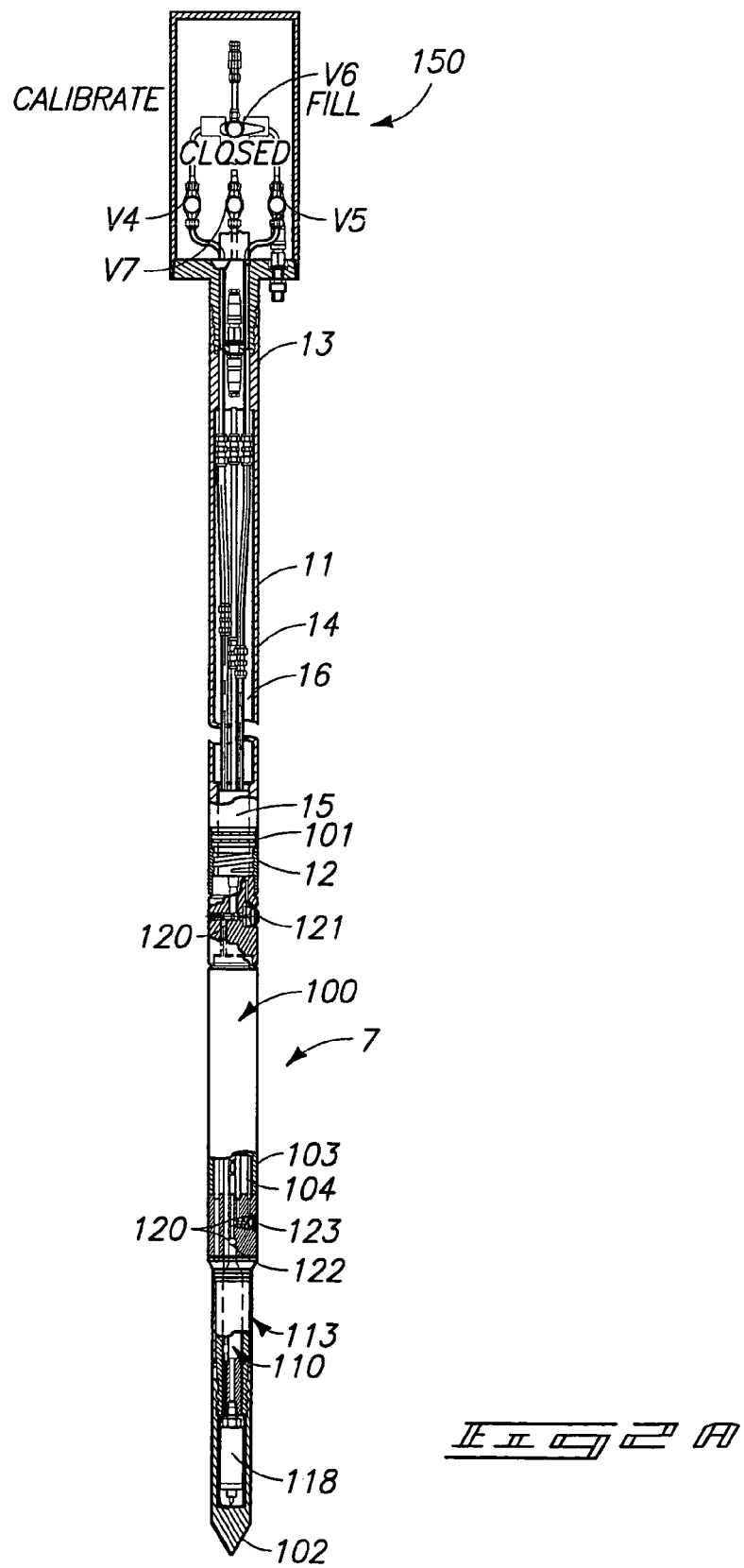

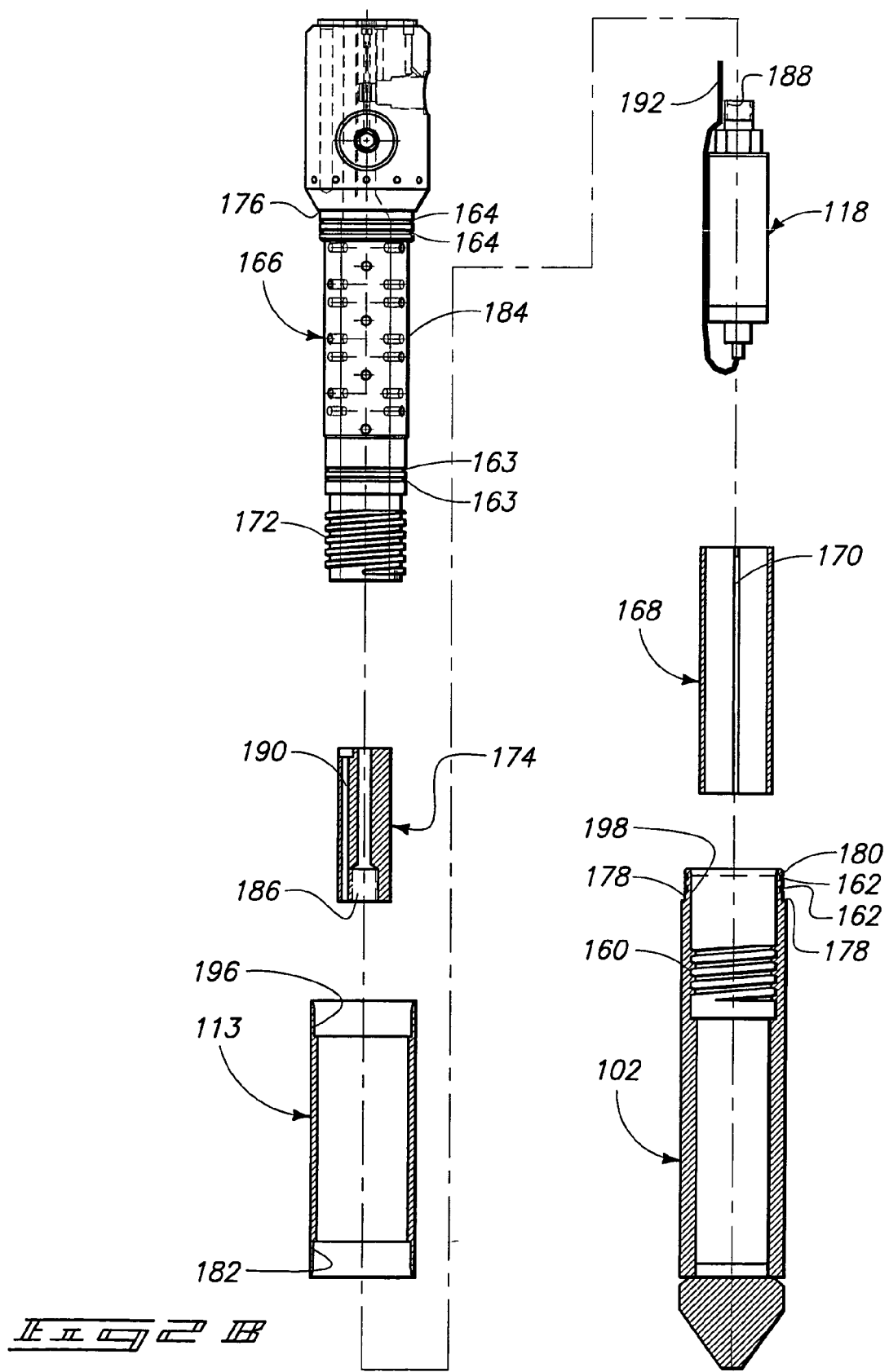

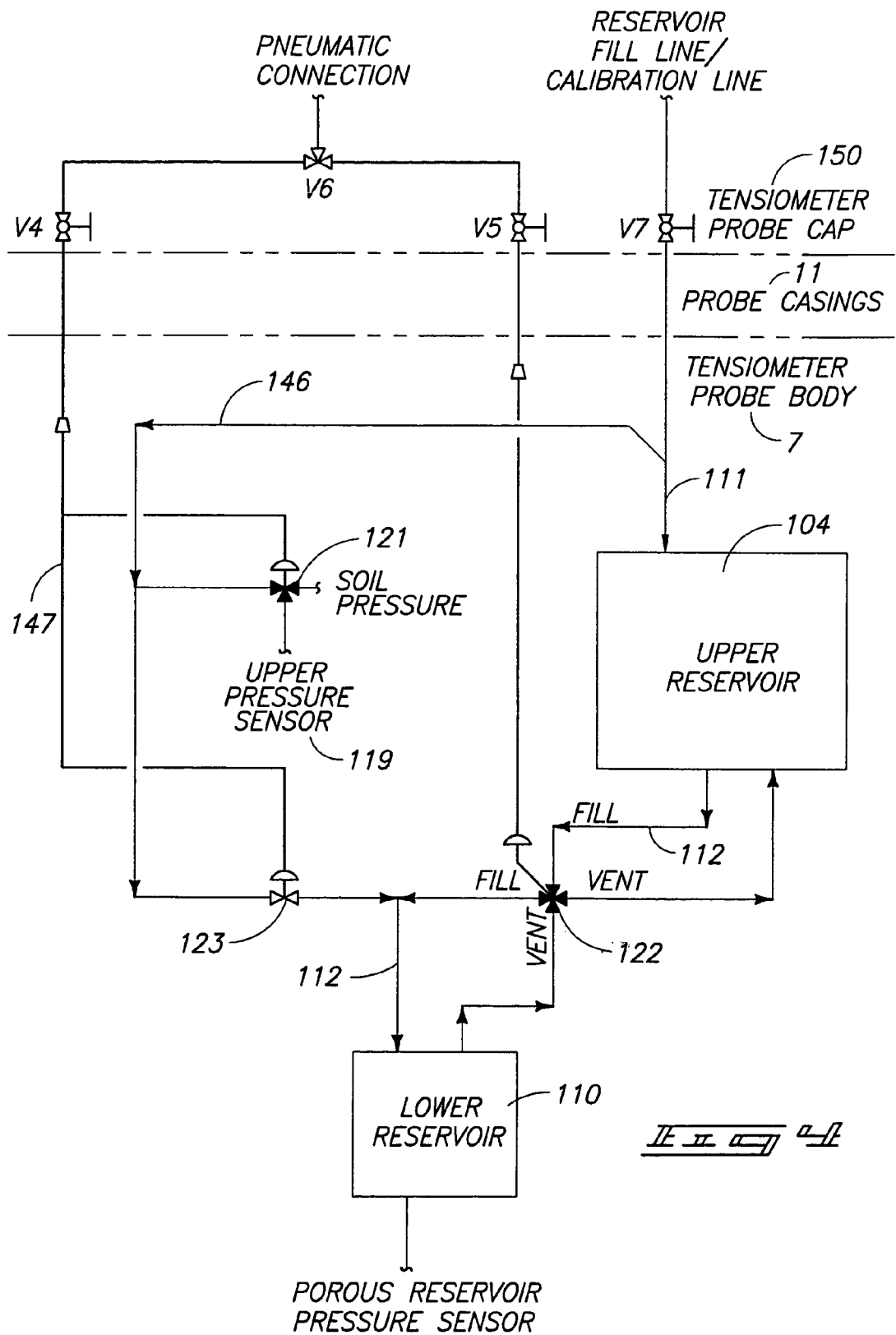

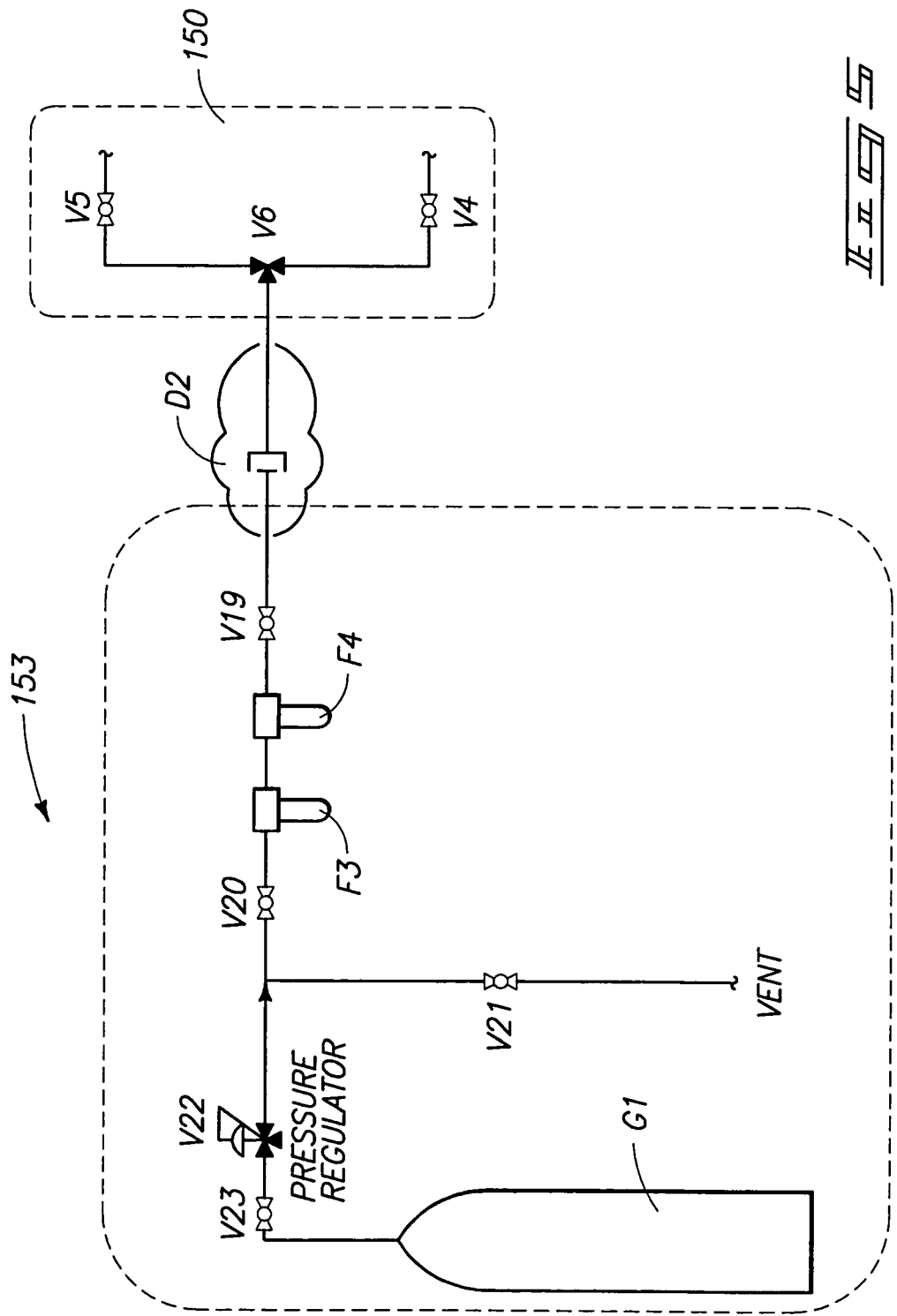

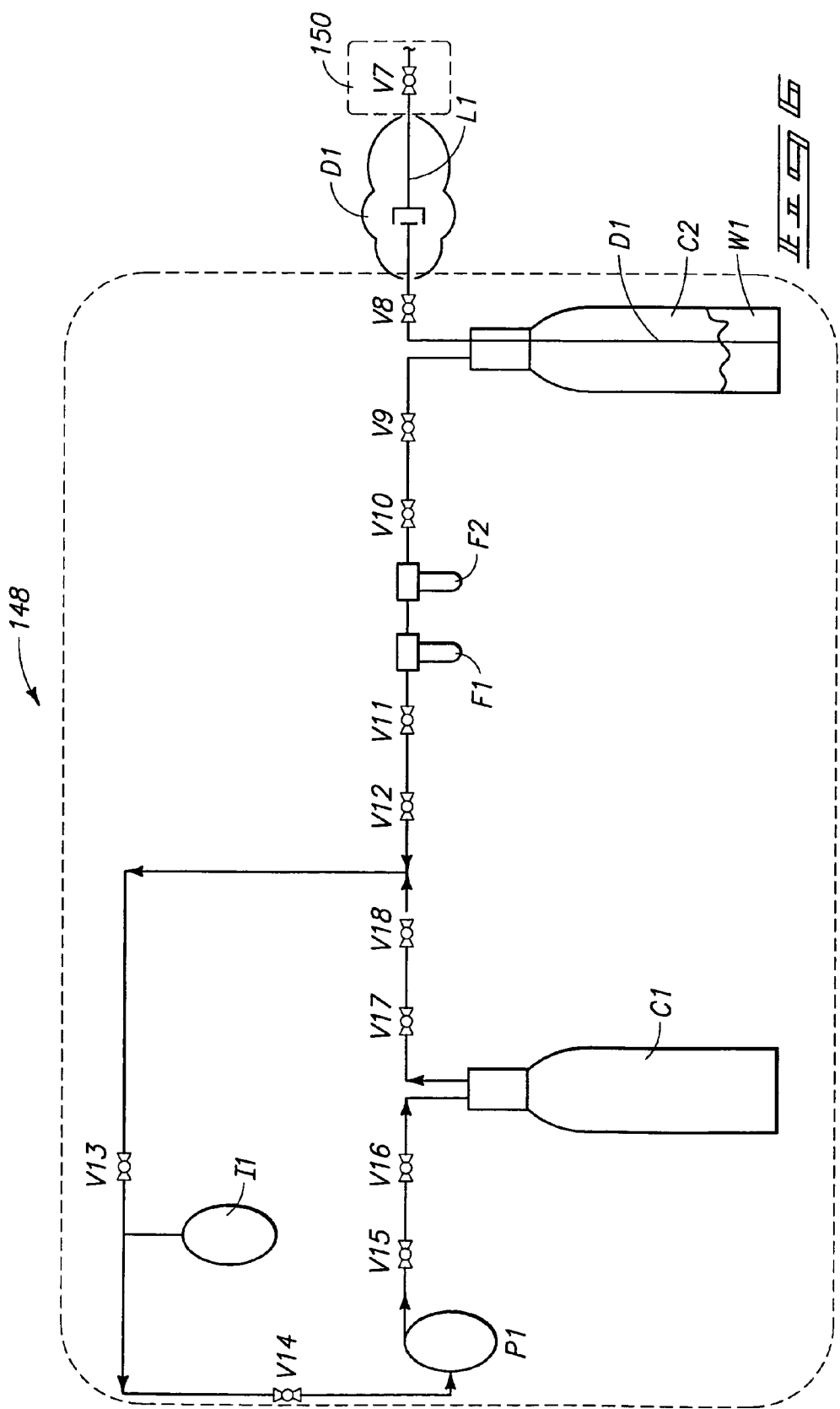

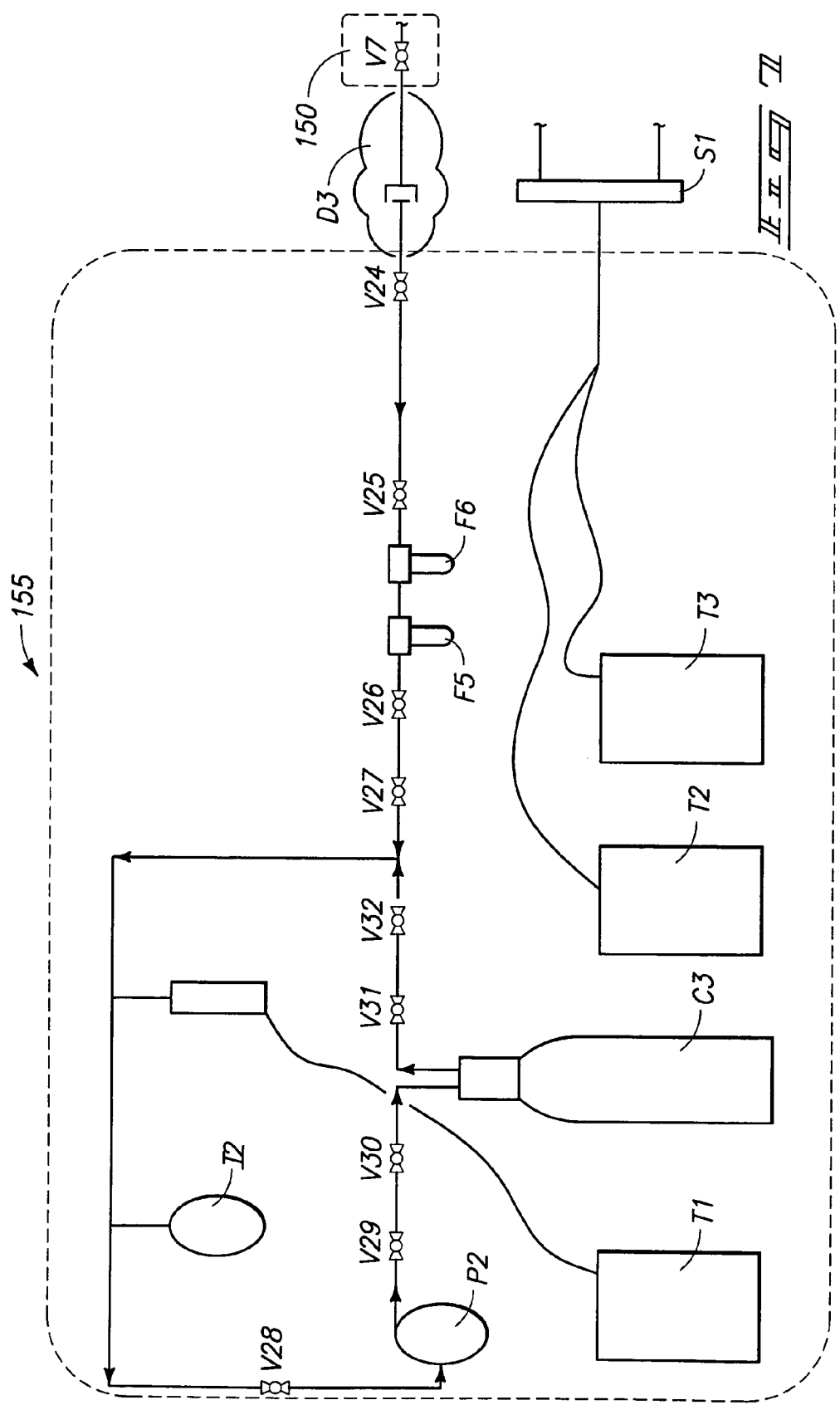

TENSIOMETER METHODS

RELATED APPLICATION

This application is a divisional of application Ser. No. 10/286,709, filed Oct. 31, 2002, now U.S. Pat. No. 6,772, 621.

GOVERNMENT RIGHTS

This invention was made with Government support under Contract DE-AC07-99D13727 awarded by the U.S. Department of Energy. The Government has certain rights in the invention.

TECHNICAL FIELD

The invention relates to methods and apparatus for subsurface testing. More specifically the invention relates to methods and apparatus for evaluation of subsurface moisture content.

BACKGROUND OF THE INVENTION

Water and associated contaminants seep into the ground and travel through a subsurface region known as the vadose zone (a region of unsaturated soil). How the water and associated contaminants move in the vadose zone, to a large degree, determines how much contamination (such as gasoline additives, agricultural chemicals, or buried nuclear waste leakage) may end up in a water supply (such as an aquifier). Therefore, gaining an understanding of how the water and associated contaminants move in the vadose zone is valuable for appropriate waste containment. Information regarding the movement of water and associated contaminants in the vadose zone is generally acquired through the use of subsurface probes or similar testing devices. Several apparatus and methods have been used to facilitate such testing and information gathering. Some of these apparatus and methods involve obtaining samples of subsurface liquids, while others test soil moisture or other parameters.

One particular type of device which has proven useful in gathering information is a tensiometer. The tensiometer is a hydrological instrument which is used to determine the moisture content of unsaturated soils or other substrates. The tensiometer measures "matric potential"—a measure of how tightly water is held under tension in an unsaturated environment. By grouping several tensiometers at different depths, water gradients can be determined. This in turn allows one to determine the direction and rate of water flow within the unsaturated substrate.

Although prior tensiometers have been useful in gathering information, such tensiometers have shortcomings which have limited their usefulness. For example, prior tensiometers typically cannot be installed in highly contaminated areas without prior excavation or drilling, and in contaminated areas such excavation or drilling is highly undesirable as it would tend to spread contamination.

Monitoring and testing to determine the movement of subsurface water and associated contaminants is particularly valuable when dealing with waste disposal sites that contain radiological contaminants or other hazards. However, as described above, placing probes into the subsurface for data collection in such sites has not been feasible, because the placing of such probes would require drilling or coring which would bring contaminated "cuttings" to the surface and would create a pathway through which contaminated emissions may escape. As a result, testing probes have typically been placed in areas around such waste sites. Unfortunately, such probe placement only provides information when the contaminants have already migrated outside of the waste disposal site area. Moreover, at the point when the contaminants have already migrated outside of the waste disposal site area, it is likely that a major contaminant plume already exists in the subsurface soil and aquifer making remediation and containment efforts much more difficult and costly.

In view of the foregoing, it would be highly desirable to provide methods and apparatus which facilitate subsurface testing in both contaminated and non-contaminated areas, while substantially avoiding these and other shortcomings of the prior devices.

BRIEF DESCRIPTION OF THE DRAWINGS

Preferred embodiments of the invention are described below with reference to the following accompanying drawings.

FIG. 1 is a front elevational view, partly in section, showing a tensiometer in accordance with one embodiment of the present invention, and also showing a portion of a probe casing.

FIG. 2A is a front elevational view, partly in section, showing a tensiometer in accordance with one embodiment of the present invention. The tensiometer cap is also shown.

FIG. 2B is an exploded view illustrating how components at the bottom of FIG. 2A are assembled together.

FIG. 4 is a schematic illustration, showing instrument piping which is used with the tensiometer of FIG. 1.

FIG. 5 is a schematic illustration, showing a pneumatic system which is used with the tensiometer of FIG. 1.

FIG. 6 is a schematic illustration, showing a water fill system which is used with the tensiometer of FIG. 1.

FIG. 7 is a schematic illustration, showing a calibration system which is used with the tensiometer of FIG. 1.

DETAILED DESCRIPTION OF THE PREFERRED EMBODIMENTS

Figure 3:
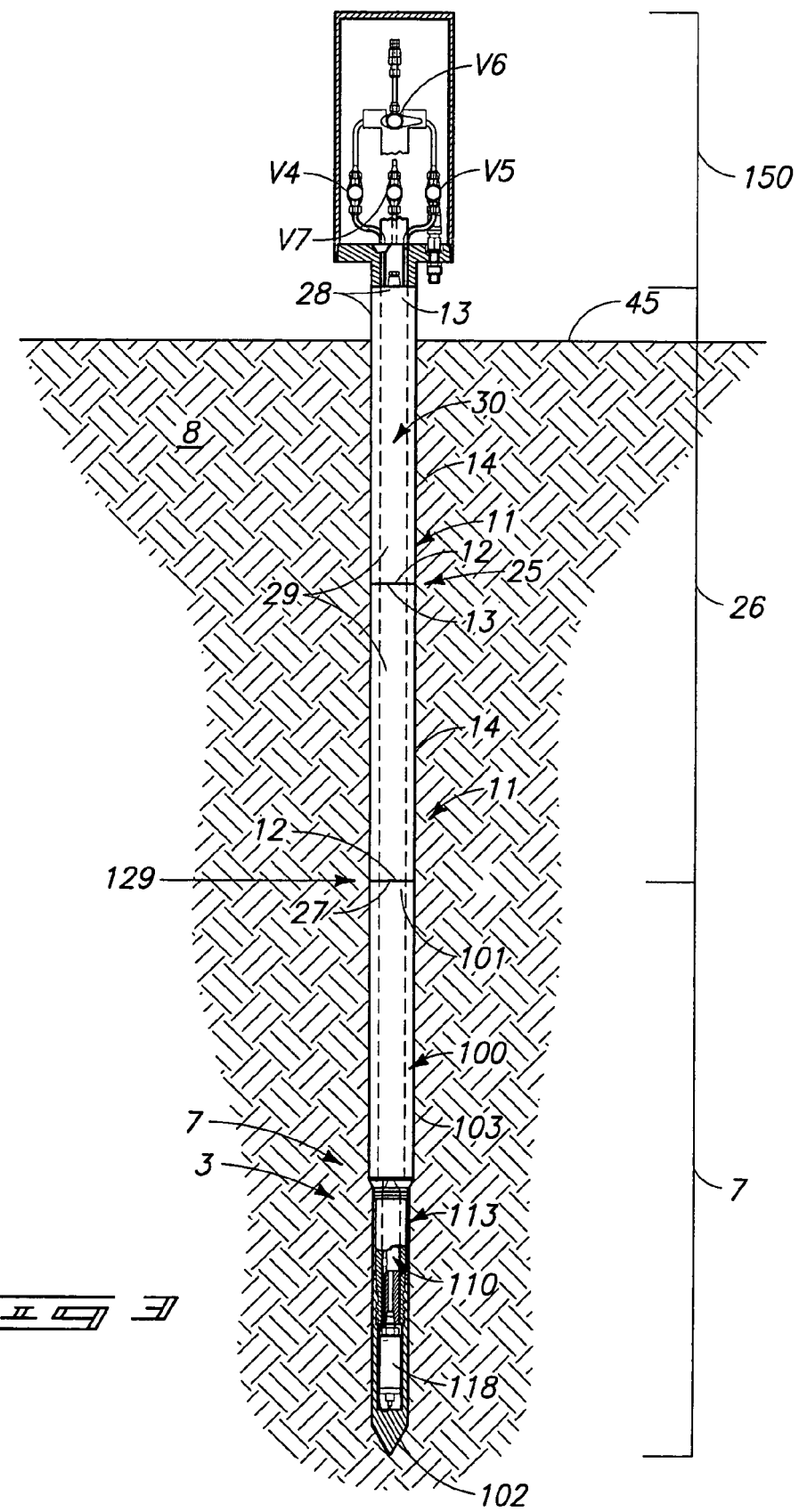
FIG. 3 is a front elevational view, partly in section, showing the probe casings of FIG. 1 and the tensiometer of FIG. 2A positioned for use in a substrate.

This disclosure of the invention is submitted in furtherance of the constitutional purposes of the U.S. Patent Laws "to promote the progress of science and useful arts" (Article 1, Section 8).

FIGS. 1–7 show a tensiometer 7 for collecting data regarding the matric potential of the ground 8. The tensiometer 7 includes a tensiometer casing 100. The tensiometer casing 100 includes a base portion 101, a tip portion 102, and a casing sidewall 103. An upper reservoir 104 is positioned within the tensiometer casing 100 as shown. A lower reservoir 110 is positioned within the tensiometer casing 100, and elevationally below the upper reservoir 104. A first fluid conduit 111 (see FIG. 4) is coupled in fluid flowing relation relative to the upper reservoir 104. In operation, the first fluid conduit 111 supplies a fluid to the upper reservoir 104. A second fluid conduit 112 couples the upper and lower reservoirs 104 and 110 in fluid flowing relation. In operation, the second fluid conduit 112 supplies the fluid from the upper reservoir 104 to the lower reservoir 110.

A membrane 113 (see FIG. 1) is coupled in fluid flowing relation relative to the lower reservoir 110. In operation, typically at least some of the fluid from the lower reservoir 110 passes through the membrane 113 as the fluid is drawn by the matric potential of the area in the ground 8 which is located adjacent to the membrane 113. The membrane 113 is a porous stainless steel membrane in the illustrated embodiment; however, alternative materials are employed in other embodiments.

FIG. 2B is an exploded view that illustrates construction details of a lower portion of the tensiometer, in one specific embodiment.

The lower spool valve body 166 has an inner cavity that slidingly receives a plug 174. In one embodiment, the plug 174 is secured (e.g., welded) to the lower spool valve body 166. The plug 174 defines the lower reservoir 110 in the lower valve body 166. The plug 174 includes threads 186 which engage corresponding threads 188 on a lower pressure sensor 118. The plug 174 also includes a conduit 190 for passing wiring 192 from the sensor 118 that is routed through to the top of the tensiometer.

The porous membrane 113 is selectively slidingly received over an outer annular surface 184 of the lower spool valve body 166 and held between an abutment surface 176 on the lower spool valve body 166 and an abutment surface 178 on the tip portion 102. During assembly, the porous membrane 113, in one embodiment, is slid over the outer annular surface 184 after the plug 174 is received in the lower spool valve body 166. The tip portion 102 includes an upper outer annual surface 180 that is slidingly received inside an inner annular surface 182 of the porous membrane 113.

The lower pressure sensor 118 is positioned within the tip portion 102 and is coupled in sensing relation relative to the lower reservoir 110. The lower pressure sensor 118 is configured to measure the matric potential of the ground 8. In one embodiment, the lower pressure sensor 118 is located in the tip portion 102 of the tensiometer casing 100. In the illustrated embodiment, the lower pressure sensor 118 is located below the lower reservoir 110 to reduce variations in pressure readings. During assembly, in one embodiment, the threads 188 of the sensor 118 are caused to engage the threads 186 of plug 174 after the porous membrane 113 has been received on the lower spool valve body 166.

A sensor sleeve assembly 168 is sliding received over the sensor 118. The sleeve assembly 168 includes a keyway 170 for passing the wiring 192. During assembly, in one embodiment, the sleeve assembly 168 is slid over the sensor 118 after the threads 188 of the sensor 118 are caused to engage the threads 186 of the plug 174.

The tip portion 102 receives the brunt of insertion forces and can therefore be damaged. The tip portion 102 includes threads 160 that selectively mate with corresponding threads 172 on a lower spool valve body 166 proximate the lower reservoir 110 (see FIG. 2B). During assembly, in one embodiment, the tip portion 102 is threaded to the lower spool valve body 166 after the sleeve assembly 186 is slid over the sensor 118. The tip portion 102 can be easily removed from the lower spool valve body 166 and replaced (or repaired) by unthreading the tip portion 102 from the lower spool valve body 166.

Similarly, the porous membrane 113 can be easily removed and replaced. To replace the porous membrane 113, the tip portion 102 is unthreaded from the lower spool valve body 166, and the porous membrane 113 is slid off of the lower spool valve body 166 and replaced. The tip portion 102 is then re-threaded to the lower spool valve body 166.

In the illustrated embodiment, a seal is provided at the interface between the tip portion 102 and the porous membrane 113. More particularly, in one embodiment, redundant outer facing o-ring seal members 162 are provided in the tip portion 102 proximate the surface 180 (see FIGS. 1 and 2B).

In the illustrated embodiment, a seal is provided at the interface between the porous membrane 113 and the lower spool valve body 166. More particularly, in one embodiment, redundant outer facing o-ring seal members 164 are provided (see FIGS. 1 and 2B) for engagement with an inner annular surface 196 of the porous membrane 113.

In the illustrated embodiment, a seal is provided at the interface between the tip portion 102 and the lower spool valve body 166. More particularly, in one embodiment, redundant outer facing o-ring seal members 163 are provided (see FIG. 2B) for engagement with an inner annular surface 198 of the tip portion 102.

In one embodiment, an upper pressure sensor 119 (FIG. 1) is operably coupled to the tensiometer casing 100. In operation, the upper pressure sensor 119 measures local soil air pressure near the lower reservoir 110. At least one sensor conduit 146 (see FIG. 1) for transmitting data is coupled to the upper and lower pressure sensors 119 and 118. In one embodiment, the upper and lower pressure sensors 119 and 118 may be individually removed and replaced as needed. In one embodiment, the lower pressure sensor 118 and upper pressure sensor 119 are "absolute" pressure sensors that reduce barometric noise from data. This type of sensor provides truer readings and removes the need for venting of the sensors to atmosphere. Therefore, no pathway to the surface is necessary for venting of the pressure sensors. Thus, a pathway for contaminates has been eliminated. However, in alternative embodiments, differential pressure sensors could be employed. A seal is also provided at the top of the porous membrane 113. More particularly, in one embodiment, redundant seals 164, such as o-rings, are provided.

The tensiometer 7 includes valves 120 which function as a substantial barrier to contaminants. One of these valves 120 is an upper calibration valve 121 which in operation is used for calibrating the upper pressure sensor 119. Another of these valves 120 is a fill valve 122. In operation, the fill valve 122 is used to selectively control the flow of fluid from the upper reservoir 104 to the lower reservoir 110. Yet another of these valves 120 is a lower calibration valve 123, which in operation is used for calibrating the lower pressure sensor 118. The use of each of these valves 121, 122, and 123 is described in detail below. In operation, the valves 120 allow the lower and upper pressure sensors 118 and 119 to be calibrated remotely while the tensiometer 7 is in use. Yet further, in operation, the valves 120 allow the tensiometer 7 to be flushed out remotely while the tensiometer 7 is in use.

The tensiometer casing 100 shown in FIGS. 1, 2A and 3 is formed of stainless steel. However, any suitable material may be used to construct the tensiometer casing 100. In one embodiment, the tensiometer casing 100 is formed of stainless steel, and is of adequate durability for installation into a substrate by direct push, by sonic drilling, or by a combination of direct push and sonic drilling.

Referring again to FIGS. 1, 2A and 3, the base portion 101 of the tensiometer casing 100 is configured to selectively couple to the first end 12 of a probe casing 11 at a base connection joint 129. Stated in other terms, the base portion 101 of the tensiometer casing 100 is configured to selectively couple to the instrument receiving end 27 of an insertion tube 26 at the base connection joint 129. The base connection joint 129 includes a base connection seal 130 which functions as a substantial barrier to contaminants.

As shown in FIG. 1, in one embodiment, the base connection seal 130 comprises a plurality of seals. More particularly, in the illustrated embodiment, the base connection seal 130 is defined by two seals or two o-ring seals 131 which function as a substantial barrier to contaminants. The base connection joint 129 includes bearing surfaces 132 which function to isolate the base connection seal 130 and to protect the base connection seal 130 from large loads as the tensiometer probe 7 is inserted into the ground 8.

As shown in FIG. 3, probe casings 11 are selectively coupled to form an insertion tube 26. The insertion tube 26 has an instrument receiving end 27 which is configured to selectively couple with the base portion 101 of the tensiometer casing 100. The insertion tube 26 also has a surface end 28 and an insertion tube wall 29. Together, the instrument receiving end 27, the surface end 28, and the insertion tube wall 29 define a central cavity 30 (shown in phantom lines).

As described above, the plurality of probe casings 11 are selectively coupled to form the insertion tube 26. In the illustrated embodiment, the insertion tube so formed has an outside diameter of less than four inches; however, other sizes are possible. The outer wall or sidewall 14 of the probe casings 11 define an outside diameter of the probe casings 11, and which is also the outside diameter of the insertion tube which is formed as the respective probe casings are selectively coupled (FIG. 3). In one embodiment, the outside diameter of the insertion tube is less than four inches. In the depicted embodiment, the outside diameter of the insertion tube is about two and one-half inches.

As shown in FIG. 1, the instrument receiving end 27 of the insertion tube 26 and the base portion 101 to the tensiometer casing 100 are configured so that they may be easily coupled. Only a portion of the insertion tube 26 is shown above the tensiometer probe 7 in FIG. 1. In one embodiment, selectively coupling the instrument receiving end 27 of the insertion tube 26 to the base portion 101 to the tensiometer casing 100 requires less than four turns to fully engage the base connection joint 129 and base connection seal 130. More particularly, in the depicted embodiment, selectively coupling the instrument receiving end 27 of the insertion tube 26 to the base portion 101 to the tensiometer casing 100 requires just two and one-half turns to fully engage the base connection joint 129 and the base connection seal 130.

As shown in FIG. 1, the insertion tube 26 functions as a conduit through which various conduits may pass. For example, in one embodiment, at least one sensor conduit 146 is coupled to the upper and lower pressure sensors 119 and 118. The sensor conduit 146 passes through the insertion tube, and in operation transmits data. In one embodiment, at least one air conduit 147 (see FIG. 4) is coupled to the valves 120 for controlling operation of the valves 120. The air conduit 147 passes through the insertion tube 26. In one embodiment, the insertion tube 26 functions as a conduit through which the first fluid conduit 111 (see FIG. 4) passes.

The insertion tube 26 and the tensiometer casing 100 are of an adequate durability for installation into the ground 8 by direct push, by sonic drilling, or by a combination of direct push and sonic drilling.

FIGS. 1–3 also depict a method of collecting data regarding a matric potential of a sample. In one embodiment, the method includes providing a tensiometer 7. The tensiometer 7 includes a porous membrane 113 (see FIGS. 1–3) comprising stainless steel, a lower reservoir 110, a first fluid conduit 111 (see FIG. 4) which couples the lower reservoir 110 in fluid flowing relation relative to the porous membrane 113, and a tensiometer casing 100 having a base portion 101. An insertion tube 26 is provided. The insertion tube 26 includes probe casings 11 which have been selectively coupled at casing joints 25. The insertion tube so formed, has an instrument receiving end 27, a surface end 28, and an insertion tube wall 29 which together define a center cavity 30. The method includes selectively coupling the instrument receiving end 27 of the insertion tube 26 with the base portion 101 of the tensiometer casing 100 at a base connection joint 129. The base connection joint 129 includes a base connection seal 130 which functions as a substantial barrier to contaminants. The insertion tube 26 and the tensiometer 7 are inserted into ground 8, so that the porous membrane 113 is in contact with the ground 8. A fluid is provided to the lower reservoir 110, so that the fluid is in contact with the porous membrane 113. The fluid is thereby exposed to a matric potential the ground 8 exerts on the fluid through the porous membrane 113. The tensiometer 7 is sealed using valves 120 which act as a substantial barrier to contaminants. The matric potential that the ground 8 exerts on the fluid is then measured using the lower pressure sensor 118.

By way of example only, methods and apparatus for adding water to the tensiometer probe 7, methods and apparatus for transferring water from the upper to lower reservoirs 104 and 110, and methods and apparatus for calibrating the tensiometer probe 7 are described below with emphasis on FIGS. 1–7.

In one embodiment, in operation, after the tensiometer probe 7 has been installed, a small amount of water (240–250 mL) is added to the upper reservoir 104 of the tensiometer 7. Thereafter, water is added to the tensiometer 7 as needed.

Referring to FIG. 6, the process of adding water to the tensiometer 7 is described in further detail. Initially, one should gather all equipment needed for the water filling system 148 (this includes a vacuum pump P1, ball valves V7–V18, disconnects, HEPA filters F1 and F2, two one liter sample containers C1 and C2 with double connection caps, tubing, pressure indicator II, and sleeving). The sampling container C2 which is positioned nearest the tensiometer cap 150 should be filled with between 240 mL and 250 mL demineralized water W1. A drawtube D1 is then installed on the cap of the sampling container C2 which holds the demineralized water W1, so that the tip of the drawtube D1 will be within touching distance of the bottom of the sample container C2. The cap and attached drawtube D1 are then installed onto sample container C2 which has been filled with the demineralized water W1.

After preparing the sample container C2, the access cover (not shown) is removed from the tensiometer cap 150 (FIGS. 2 and 3). The drawtube D1 is then connected to the tensiometer line L1 as shown. The vacuum pump P1, HEPA filters F1 and F2, and the two sample containers C1 and C2 are also connected into the water filling system 148 as shown.

After the vacuum pump P1, HEPA filters F1 and F2, and the two sample containers C1 and C2 have been connected into the water filling system 148 as described above, valves V8 through V18 of the water filling system 148 are closed. After valves V8 through V18 of the water filling system have been closed, the water filling system 148 should be sleeved and connected to the fill/calibration line quick disconnect D1 on the tensiometer cap 150 and ensure the connection and sleeve are secure. After this has been completed, valves V8 through V13, V15, and V16 on the water filling system 148 should be opened. Valve V7 on the tensiometer cap 150 should also be opened (FIGS. 2A, 3, 4 and 6).

The vacuum pump P1 should be started. Then, while observing pressure indicator I1, the valve V14 on the water filling system 148 should be slowly opened to allow system pressure to reduce. When the system pressure has reduced to a pressure of 6 to 7 psia (12 to 15 in. Hg Vacuum) on pressure indicator I1, valve V14 and V16 should be closed and the vacuum pump P1 stopped.

After stopping the vacuum pump, P1, valve V17 on the water filling system 148 should be opened. Then, valve V18 on the water filling system 148 should be slowly opened to begin transferring water W1 from the sample container C2 to the tensiometer probe 7. The water W1 should be vacuum drawn and pressure assisted from the sample container C2 filled with demineralized water W1 to the tensiometer probe 7.

One should wait a minimum of 10 minutes or until water transfer is complete. If water W1 is not drawn into the tensiometer probe 7, then valves V7 through V18 should be closed, and the water fill system 148 inspected for leaks or other problems. Any needed repairs should be made before repeating the filling process which was described above.

When as much water W1 as possible has been transferred from the sample container C2 to the tensiometer probe 7, valve V7 on the tensiometer cap 150 should be closed. After closing valve V7, valves V14 and V16 on the water filling system 148 should be opened. After opening valves V14 and V16 on the water filling system 148, the pressure will equilibrate. After the pressure has equilibrated, valves V8 through V18 on the water filling system 148 should be closed, and the water filling assembly 148 should be disconnected from the fill/calibration quick disconnect D1 on the tensiometer cap 150.

Water should be present in the tensiometer upper reservoir 104 before water may be transferred to lower reservoir 110. Additionally, the water in the upper reservoir 104 should be transferred to the lower reservoir 110 before data can be obtained, and when deemed necessary from electrical feedback data. The upper reservoir 104 is filled as described above in connection with the description of adding water to the tensiometer.

FIG. 5 illustrates transferring water to the lower reservoir 110. Before doing so, equipment for pneumatic system 153 should be gathered (ball valves V4–V6 and V19–V23, inert gas cylinder G1 and pressure regulator, HEPA filters F3 and F4, sleeving, and disconnects). Each of these items is connected as shown in FIG. 5.

Before transferring water to the lower reservoir 110, the inert gas cylinder G1 pressure regulator V22 should be closed, and it should be determined that there is no gas pressure in the pneumatic system 153. After it has been verified that there is no gas pressure in the pneumatic system 153, the three-way ball valve V6 on the tensiometer cap 150 should be rotated to the fill position as marked (FIG. 2A). Then valve V5 on the tensiometer cap 150 should be opened. Then, the inert gas cylinder shut-off valve V23 on the pneumatic system 153 should be opened. Gas pressure should be applied gradually to avoid damaging the tensiometer valve 122. In one embodiment, a pressure over 100 psig may damage the tensiometer valve 122. The gas cylinder regulator V22 should be slowly opened until 50 to 55-psig is applied to the pneumatic system 153. After a minimum of 2 minutes, the inert gas cylinder shut-off valve V23 should be closed. After the inert gas cylinder G1 shut-off valve V23 has been closed, valve V21 on the pneumatic system 153 should be opened to bleed/vent-off the gas pressure. Then valve V5 on the tensiometer cap 150 should be closed. The 3-way valve V6 on tensiometer cap should be turned to the closed position (FIG. 2A). Valve V21 on the pneumatic system 153 should then be closed. Valves V19, V20, and V22 on pneumatic system 153 should then be closed. At this point one may disconnect the pneumatic system 153 from the pneumatic line quick disconnect D2 on the tensiometer cap 150.

Calibration of tensiometer sensors will now be described. Before checking the calibration of the lower pressure sensor 118, the lower reservoir 110 should be filled with water as described above. Before beginning calibration of the upper and lower pressure sensors 119 and 118, all equipment needed for pneumatic system 153 should be gathered (ball valves V4–V6 and V19–V23, inert gas cylinder G1 and pressure regulator, HEPA filters F3 and F4, sleeving, and disconnects). Each of these items are connected as shown in FIG. 5. Additionally, before beginning pressure sensor calibration, all equipment needed for the calibration system 155 (FIG. 7) should be gathered. This includes a vacuum pump P2, ball valves V24–V32, disconnects, HEPA filters F5 and F6, a sample container C3 with double connection cap, tubing, pressure indicator I2, sleeving, calibration tools T1–T3, calibrated pressure sensor, and probe interface electrical connector.

The vacuum pump P2, HEPA filters F5 and F6, sample container C3, calibration tools T1–T3, and other equipment should be connected as shown in FIG. 7. Then the tensiometer cap cover should be removed (not shown) from the tensiometer cap 150. Next, the tensiometer sensors 118 and 119 (see FIG. 1) should be disconnected from the data logging system at the bottom of the tensiometer cap 150.

The inert gas cylinder G1 pressure regulator V22 (see FIG. 5) on the pneumatic system 153 should be closed, and there should be no gas pressure. Then valves V19 and V20 are opened. The pneumatic system 153 is sleeved and connected to the pneumatic connection quick disconnect D2 on the tensiometer cap 150. It should be verified that connection and sleeve are secure.

At this point, valves V24 through V32 are closed on the calibration system 155. Then the calibration system 155 is sleeved and connected to the fill/calibration line quick disconnect D3 on the tensiometer cap 150. It should be verified that the connection and sleeve are secure.

The calibration tool T1 is connected to the calibration system 155. The calibration tools T2 and T3 are connected to the tensiometer probe sensor connector S1, as shown in FIG. 7. The identity of the calibration tool connected to upper pressure sensor 119 is determined along with the identity of the calibration tool connected to the lower pressure sensor 118.

Valve V6 on the tensiometer cap 150 is turned to the calibrate position (FIG. 2A). Then valve V4 on the tensiometer cap 150 is turned to the open position. The inert gas cylinder G1 shut-off valve V23 on the pneumatic system 153 is opened. Gas pressure should be applied gradually to avoid damaging any of the tensiometer valves 120. In one embodiment, pressure over 100 psig may damage the tensiometer valves 120. Then, the gas cylinder G1 regulator V22 is slowly opened until about 65 to 70-psig (but not more than 100 psig) is applied to the pneumatic system 153.

Valves V24 through V27, V29, and V30 on the calibration system 155 are then opened. Valve V7 on the tensiometer cap 150 (FIG. 7) is then opened.

Multiple stepped down vacuum pressure readings should be obtained for calibration of the tensiometer pressure sensors 118 and 119. A total of 7.5 to 8 psi (15.3 to 16.3 inch Hg) vacuum below atmospheric pressure should not be exceeded. The vacuum pump P2 should be started, and while observing pressure indicator I2, valve V28 on the calibration system 155 should be slowly opened to reduce system pressure. Valve V28 should be closed and the vacuum pump P2 shut off after a pressure drop is shown on indicator I2. After waiting, e.g. a minimum of 30 seconds, the standard and calibration tool readings are measured and recorded to their respective upper and lower pressure sensors 119 and 118.

The steps outlined in the paragraph above are repeated in one embodiment, until a reasonable number (e.g. a minimum of five each) standard and tensiometer pressure sensor readings have been taken over a maximum of 8 psi (16.3 inches Hg) vacuum range. After all standard and calibration pressure readings are measured and recorded, valve V31 should be opened. After opening V31, valve V32 is slowly opened. Valve V32 should be opened slowly to prevent shock on system which could cause damage to the pressure sensors 118 and 119. Then the calibration system 155 comes to equilibrium pressure. After the calibration system 155 has come to equilibrium pressure, valves V24 through V32 should be closed. Valve V7 on the tensiometer cap 150 should then be closed.

The inert cylinder shut-off valve V22 and the pressure regulator valve V23 should then be closed. Bleed valve V21 on the pneumatic system 153 is opened to bleed/vent-off the gas pressure. Valve V4 on the tensiometer cap 150 is then closed. The 3-way ball valve V6 should be turned to the closed position on the tensiometer cap. Valves V19 and V20 on the pneumatic system 153 should then be closed. Then valve V21 on the pneumatic system 153 should be closed. The pneumatic system 153 is then disconnected from the pneumatic line quick disconnect D2 on the tensiometer cap 150. The calibration system 155 is then disconnected from the fill/calibration line quick disconnect D3 on the tensiometer cap 150. The pneumatic and calibration systems 153 and 155 are then removed from the tensiometer cap 150. The tensiometer probe cap cover (not shown) is reinstalled, and the tensiometer probe 7 upper and lower pressure sensors 119 and 118 are reconnected to the data logging system.

While specific pressure values and ranges (i.e., psia, psi, inches Hg, etc.) were given above, various are, of course, possible depending on the valves and hardware used.

A tensiometer has been disclosed that provides an advantageous spool valve design. In one embodiment, three pneumatically operated spool valves define isolation chambers for operation and calibration. Refilling the tensiometer using the spool valves does not change readings significantly. The spool valves operate under low pressure gas which results in a more reliable pneumatic system. The spool valves fail in safe positions, preventing contamination migration into the instrument and to land surface. The spool valves are used in a unique configuration that allows filling and in-place calibration. The spool valves are replaceable. The tensiometer supports transducers that measure both soil gas pressure and soil water pressure at the measurement point. The transducers are insulated from loads used to install the tensiometer. The transducers do not see the driving loads associated with installation into the ground, which prevents damage or shifting of the sensor. The thread on the tip top has redundant seals to prevent contamination from entering non-measured areas of the tensiometer. Tubing connections at ground surface are minimized for operation or maintenance of the tensiometer. The lower reservoir of the tensiometer is vented to the upper reservoir to ensure maximum filling of the lower reservoir during the refilling process. The porous stainless steel membrane has redundant seals and can be replaced if instruments are to be removed and reused. A calibration technique, using multiple valves, has been disclosed which permits recording of precisely known values. The calibration system is closed so there is no risk of spreading of contaminates. The entire instrument is put in place with one action (multiple parts are not used). If contamination is present within or from the instrument, filling it with water washes the contamination back to the upper water reservoir.

The invention provides robust tensiometers that are particularly useful for driving into highly contaminated waste, as well as other uses. The tensiometers can be driven into difficult materials (e.g., hardened soils, concrete, steel, other metals, etc.) that would typically damage other tools. In the illustrated embodiments, small diameter designs are employed that require less energy for installation into a sample. Reduced energy requirements allow for smaller driving equipment resulting in lower cost.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of collecting data regarding a matric potential of a media, comprising:

providing a tensiometer including a porous membrane comprising stainless steel, a reservoir, a first fluid conduit which couples the reservoir in fluid flowing relation relative to the porous membrane, and a tensiometer casing having a base portion, and a tip portion, the tip portion being removable and replaceable;

providing a valve member defining the reservoir, the valve member including an outer annular surface, wherein the membrane includes an inner annular surface selectively slidingly received over the outer annular surface of the valve member, wherein the tip portion is selectively threadedly connected to the valve member, and wherein the membrane is held in place between the tip portion and the valve member when the tip portion is threaded to the valve member body;

providing an insertion tube comprising a plurality of probe casings which have been selectively coupled at casing joints, the casing joints including a seal which functions as a substantial barrier to contaminants, the insertion tube having an instrument receiving end, a surface end, and an insertion tube wall which together define a center cavity;

selectively coupling the instrument receiving end of the insertion tube with the base portion of the tensiometer casing at a base connection joint, the base connection joint including a base connection seal which functions as a substantial barrier to contaminants;

inserting the insertion tube and the tensiometer into a media, so that the porous membrane is in contact with the media;

providing the reservoir with a fluid, wherein the fluid is in contact with the porous membrane, and wherein the fluid is exposed to a matric potential the media exerts on the fluid through the porous membrane;

sealing the tensiometer using a plurality of valves, which act as a substantial barrier to contaminants; and measuring the matric potential the media exerts on the fluid.

2. The method of claim 1, wherein inserting the insertion tube and the tensiometer into a media comprises using direct push.

3. The method of claim 1, wherein inserting the insertion tube and the tensiometer into a media comprises using sonic drilling.

4. The method of claim 1, wherein inserting the insertion tube and the tensiometer into a media comprises using a combination of direct push and sonic drilling.

5. The method of claim 1, wherein the tensiometer includes an upper reservoir positioned within the tensiometer casing, above the first mentioned reservoir, and a pressure sensor positioned within the tensiometer casing, and which is configured to in operation measure the matric potential of the sample, the pressure sensor being located below the first mentioned reservoir within the tip portion of the tensiometer casing to reduce variations in pressure reading, wherein the membrane is coupled in fluid flowing relation relative to the first mentioned reservoir, and wherein, in operation, the fluid from the first mentioned reservoir passes through the membrane as it is drawn by a matric potential of a sample adjacent to the membrane.

6. A method for collecting data regarding a matric potential of a media, comprising:

providing a tensiometer having a stainless steel tensiometer case, an upper reservoir positioned within the tensiometer casing, a lower reservoir positioned within the tensiometer casing, below the upper reservoir, a fluid conduit coupled in fluid flowing relation relative to the upper reservoir, and which, in operation, selectively supplies a fluid to the upper reservoir, a fluid conduit which couples the upper and lower reservoirs in fluid flowing relation, and which, in operation, selectively supplies fluid from the upper reservoir to the lower reservoir, and a pressure sensor positioned within the tensiometer casing, and which is configured to, in operation, measure the matric potential of the sample, the pressure sensor being located below the lower reservoir within the tip portion of the tensiometer casing to reduce variations in pressure reading, wherein the membrane is coupled in fluid flowing relation relative to the lower reservoir, and wherein, in operation, the fluid from the lower reservoir passes through the membrane as it is drawn by a matric potential of a sample adjacent to the membrane, the stainless steel tensiometer casing comprising a removable and replaceable tip portion which includes a porous stainless steel membrane through which a matric potential of a media is sensed, in operation:

driving the tensiometer into the media using an insertion tube comprising a plurality of probe casing which are selectively coupled to form the insertion tube as the tensiometer is progressively driven deeper into the media, wherein the porous stainless steel membrane is in contact with the media; and sensing the matric potential the media exerts on the porous stainless steel membrane.

7. The method of claim 6 wherein the tensiometer includes a valve member defining the lower reservoir, the valve member including an outer annular surface, wherein the membrane includes an inner annular surface selectively slidingly received over the outer annular surface of the valve member, wherein the tip portion is selectively threadedly connected to the valve member, and wherein the membrane is held in place between the tip portion and the valve member when the tip portion is threaded to the valve member body.

8. The method of claim 6 wherein the tensiometer includes an upper pressure sensor operably coupled to the tensiometer casing and which, in operation, measures local soil air pressure near the lower reservoir, and wherein the plurality of valves include an upper calibration valve for calibrating the upper pressure sensor, a fill valve for selectively controlling fluid flow from the upper reservoir to the lower reservoir, and a lower calibration valve for calibrating the first mentioned pressure sensor.

* * * * *